(12) United States Patent
Gluckman et al.

(10) Patent No.: US 7,112,570 B2
(45) Date of Patent: Sep. 26, 2006

(54) GPE ANALOGS

(75) Inventors: Peter Gluckman, Auckland (NZ); Tajrena Alexi, Auckland (NZ)

(73) Assignee: Neuren Pharmaceuticals, Ltd., Auckland (NZ)

( * ) Notice: Subject to any disclaimer, the term of this patent is extended or adjusted under 35 U.S.C. 154(b) by 0 days.

(21) Appl. No.: 10/362,266

(22) PCT Filed: Aug. 24, 2001

(86) PCT No.: PCT/US01/41883

§ 371 (c)(1), (2), (4) Date: Jun. 11, 2003

(87) PCT Pub. No.: WO02/16408

PCT Pub. Date: Feb. 28, 2002

(65) Prior Publication Data

US 2004/0014674 A1   Jan. 22, 2004

(30) Foreign Application Priority Data

Aug. 24, 2000 (NZ) ...................... 506534

(51) Int. Cl.
*A61K 38/06* (2006.01)
*C07K 5/083* (2006.01)

(52) U.S. Cl. ...................... 514/18; 530/331
(58) Field of Classification Search ............. 514/18; 530/331
See application file for complete search history.

(56) References Cited

U.S. PATENT DOCUMENTS

| 4,906,614 A | 3/1990 | Giertz et al. ................. 514/18 |
| 5,750,376 A | 5/1998 | Weiss et al. ............. 435/69.52 |
| 5,853,695 A * | 12/1998 | Srivastava et al. ......... 424/1.65 |
| 5,965,536 A * | 10/1999 | Cohen et al. .................. 514/17 |
| 5,965,603 A * | 10/1999 | Johnson et al. .............. 514/450 |
| 6,310,093 B1 * | 10/2001 | Newcomb .................... 514/496 |
| 6,342,585 B1 | 1/2002 | Grossman ................... 530/351 |

FOREIGN PATENT DOCUMENTS

| EP | 0366 638 | 5/1990 |
| EP | 0 357 240 B1 | 1/1993 |
| FR | 2 707 170 | 1/1995 |
| WO | WO 91/19006 A1 * | 12/1991 |
| WO | WO 93/08828 | 5/1993 |
| WO | WO 93/21216 | 10/1993 |
| WO | WO 94/23754 | 10/1994 |
| WO | WO 95/17204 | 6/1995 |
| WO | WO 96/40871 | 12/1996 |
| WO | WO 97/00688 A1 * | 1/1997 |
| WO | WO 97/17090 | 5/1997 |
| WO | WO 97/47735 | 12/1997 |
| WO | WO 98/16242 | 4/1998 |
| WO | WO 00/13650 | 3/2000 |

* cited by examiner

*Primary Examiner*—Jeffrey Edwin Russel
(74) *Attorney, Agent, or Firm*—Fliesler Meyer LLP (57) ABSTRACT

The invention relates to GPE analogs, particularly GPE analogs capable of inducing an equivalent physiological effect to GPE within a patient. Such GPE analogs include peptides where the Gly of Gly-Pro-Glu is replaced by any of Ala, Ser, Thr, or Pro; where the Pro of Gly-Pro-Glu is replaced by any of Ala, Ser, Thr, or Gly; and where the Glu of Gly-Pro-Glu is replaced by any of Asn, Asp, or Gln. The GPE analogs of the invention have application in any method of therapy or prophylaxis in which GPE has application. These applications include the treatment of acute brain injury and neurodegenerative disease, including but not limited to injury or disease in the CNS. The GPE analogs will normally be administered as part of a pharmaceutical composition or preparation.

21 Claims, 4 Drawing Sheets

GPE ANALOGS

RELATED APPLICATIONS

This application claims priority under 35 U.S.C. §371 to PCT/US01/41883, having an International Filing Date of Aug. 24, 2001, which claimed priority to New Zealand Application Ser. No. 506,534, filed Aug. 24, 2000, Each of the above applications is herein incorporated fully by reference.

This invention relates to GPE analogs.

BACKGROUND

GPE is a tri-peptide consisting of amino acids Gly-Pro-Glu. It and its di-peptide derivatives Gly-Pro and Pro-Glu were first disclosed by Sara et al in EP 0366638. Sara et al disclosed that GPE is effective as a neuromodulator (able to affect the electrical properties of neurons).

The applicants have also established that GPE has neuroprotective properties and that it therefore has utility in the prevention or inhibition of neural cell death (WO 95/17204).

The nervous system contains neural cells and glial cells. Glial cells, including astrocytes, microglia, Schwann cells in the peripheral nervous system and oligodendrocytes in the central nervous system, often aid neural cells and neural activity by providing support and assistance to neural cells through means including anatomical configuration, metabolic activity, and physiological function.

It is generally towards new molecules which mimic the functionality of GPE that the present invention is directed. These molecules, which are termed herein "GPE analogs" have application on an equivalent basis to GPE, including in treating and/or preventing neural damage following insult.

SUMMARY OF INVENTION

Accordingly, in a first aspect, the present invention provides a molecule which:
  (i) has a neural binding-site profile which is at least substantially equivalent to GPE; and
  (ii) which has a neural bioactivity profile which is at least substantially equivalent to that of GPE, said molecule being other than GPE or its di-peptide derivatives Gly-Pro and Pro-Glu.

Preferably, the molecule also has an ability to cross the blood brain barrier in humans which is at least substantially equivalent to GPE.

In a further aspect, the present invention provides pharmaceutical compositions, particularly those adapted for peripheral or intrathecal administration to a human patient, which comprise a molecule as defined above.

In yet a further aspect, the invention provides a method of inducing a neuroprotective effect in a patient for therapy and/or prophylaxis which comprises the step of administering a molecules and/or a pharmaceutical composition as defined above to said patient.

While the present invention is broadly as defined above, it will be appreciated by those persons skilled in the art that it also includes embodiments of which the following description provides examples. In particular, a better understanding of the present invention may be obtained through reference to the accompanying drawings in which:

DESCRIPTION OF THE INVENTION

As outlined above, the invention is broadly directed to molecules which are GPE analogs. Such molecules will normally be structurally related to GPE and will in each case be capable of inducing an equivalent physiological effect to GPE within a patient.

Fundamental to the invention is the recognition that it is possible to vary the structure, presentation and/or amino acid sequence of a protein while retaining substantially equivalent functionality. For example, a protein can be considered a functional equivalent of another protein for a specific function if the equivalent protein is immunologically cross-reactive with the original protein. The equivalent can be, for example, a fragment of a protein, a fusion of the protein with another protein or carrier, or a fusion of a fragment with additional amino acids. For example, it is possible to substitute amino acids in a sequence with equivalent amino acids using conventional techniques. Groups of amino acids normally held to be equivalent are:
  (a) Ala, Ser, Thr, Pro, Gly;
  (b) Asn, Asp, Glu, Gln;
  (c) His, Arg, Lys;
  (d) Met, Leu, Ile, Val; and
  (e) Phe, Tyr, Trp.

Thus, since GPE is the tripeptide Gly-Pro-Glu, GPE analogs include substitutions where the Gly of Gly-Pro-Glu is replaced by any of Ala, Ser, Thr, or Pro; where the Pro of Gly-Pro-Glu is replaced by any of Ala, Ser, Thr, or Gly; and where the Glu of Gly-Pro-Glu is replaced by any of Asn, Asp, or Gln. All of these equivalent molecules constitute GPE analogs of the invention.

The probability of one amino acid sequence being functionally equivalent to another can be measured by the computer algorithm BLASTP (Altschul et al 1990 *J. Mol. Biol.* 215: 403–410).

Further analogs in accordance with the invention include GPE amides and stearates. More particularly, specific analogs include the following:
  GPE amide
  GPE stearate
  Gly-Pro-D-glutamate (GP-D-E)
  Gly-Pro-Thr (GPT)
  Gly-Glu-Pro (GEP)
  Glu-Gly-Pro (EGP)
  Glu-Pro-Gly (EPG), all of which can be readily synthesized using standard techniques.

Additional GPE analogs in accordance with the present invention will be characterized by their being able to meet the following criteria:
  having a neural binding-site profile which is at least substantially equivalent to GPE
  having a neural bioactivity profile which is at least substantially equivalent to GPE
  and desirably, although not essentially, having an ability to cross the blood brain barrier (including in the absence of neural insult) which is at least substantially equivalent to GPE.

Figure 1:
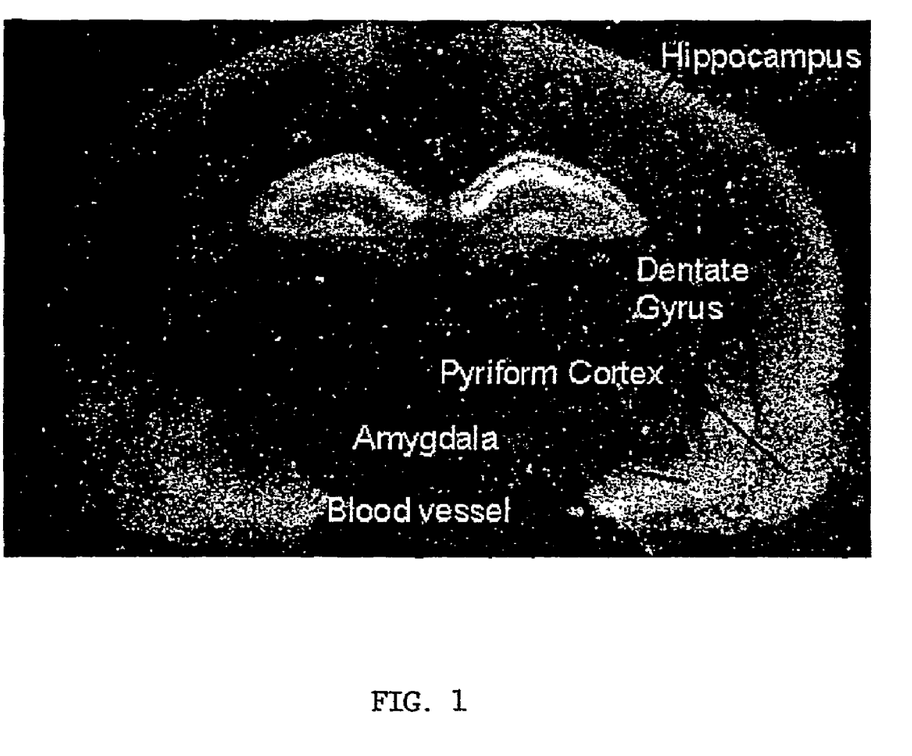
FIG. 1 shows the binding site distribution of $^3$H-Me-GPE in the rat-brain.
Figure 2:
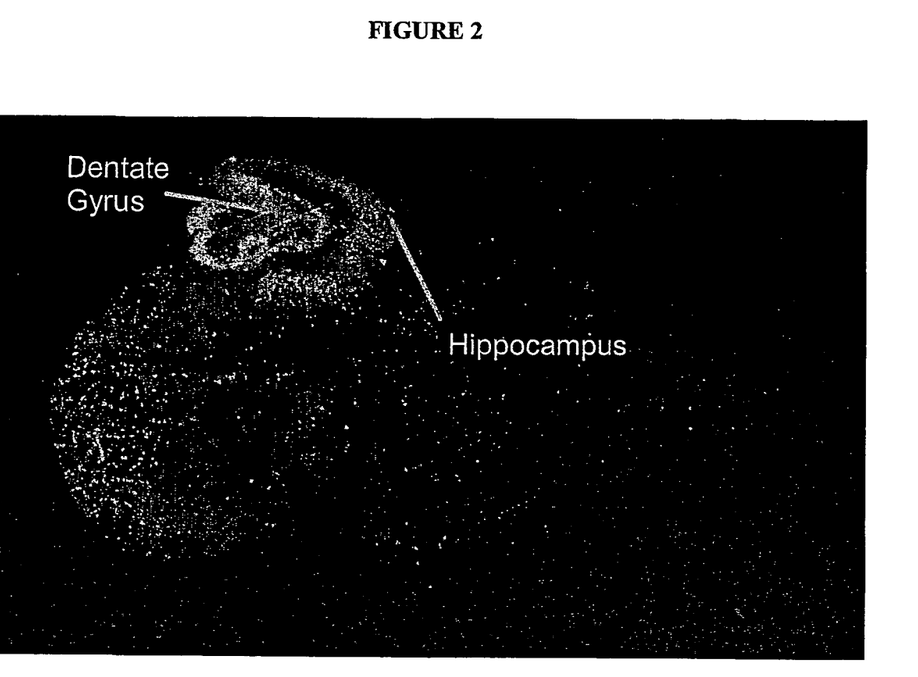
FIG. 2 shows the binding site distribution of $^3$H-Me-GPE in the human brain.

The neural binding-site profile for GPE has been determined as per Experiment 1 and is shown in FIGS. 1 and 2.

The ability of a candidate GPE analog to cross the blood brain barrier can be determined, and compared to passage rates for GPE, by following the procedures as set out in Experiment 2. In particular, the accumulation of the candidate analog can be measured 60 minutes following cardiac administration for ready comparison with GPE.

The neural bioactivity profile of a candidate GPE analog can be determined, and compared to that of GPE, by following the procedures set out in Experiment 3.

It is herein disclosed that GPE analogs can reduce neuronal cell loss due to damage caused by an insult. An insult is damage, injury or stress that may lead to death or dysfunction of nervous or glial cells or tissues. GPE analogs have application in any method of therapy or prophylaxis in which GPE has application. These include the treatment of acute brain injury and neurodegenerative disease, including but not limited to injury or disease in the CNS. For example, GPE analogs may be used in the treatment of multiple sclerosis. Such treatment may be acute (e.g., mainly directed to treating present symptoms) or may be chronic (e.g., mainly directed towards curing the disease, or towards preventing progression of the disease and long-term amelioration of symptoms). A protective effect due to administration of a GPE analog prior to the insult is termed a prophylactic effect, and a protective effect due to administration of a GPE analog during or after the insult is termed a resuscitative effect. It will be appreciated that the protective effects of GPE analogs, whether prophylactic or resuscitative, may be due to actions of GPE analogs on the neural cells themselves, on glial cells, or on cells of both types.

GPE analogs can be used in the manufacture of medicaments or pharmaceutical preparations for the treatment of medical conditions, including medical conditions resulting from neural injury or disease. Thus, GPE analogs can be administered as part of a medicament or pharmaceutical preparation. This can involve combining GPE analogs with any pharmaceutically appropriate carrier, adjuvant or excipient. The selection of the carrier, adjuvant or excipient will of course usually be dependent upon the route of administration to be employed.

The administration route can vary widely. GPE analogs may be administered in different ways, including subcutaneously, intraperitoneally, intravenously and intracerebroventricularly. GPE analogs may be administered directly to a site of injury or of possible injury; for example, directly into the parenchyma of the brain or spinal cord. This can be achieved by any appropriate direct administration route. Examples of suitable methods include administration by lateral cerebroventricular injection or through a surgically inserted shunt into the lateral cerebroventricle of the brain of the patient. Alternatively, GPE analogs may be administered to a location near to a site of injury or of possible injury; or to a body cavity in contact or fluid communication with a site of injury or of possible injury (such as, e.g., a cerebral ventricle or to the cerebrospinal fluid bathing the spinal cord).

In addition, the ability of the GPE analogs to cross the blood brain barrier allows them to be administered peripherally to a patient in need of treatment in the brain. The peripheral application may be the way of choice because then there is no direct interference with the central nervous system.

Any peripheral route of administration known in the art can be employed. These can include parenteral routes for example injection into the peripheral circulation, subcutaneous, intraorbital, ophthalmic, intraspinal, intracisternal, topical, infusion (using eg. slow release devices or minipumps such as osmotic pumps or skin patches), implant, aerosol, inhalation, scarification, intraperitoneal, intracapsular, intramuscular, intranasal, oral, buccal, pulmonary, rectal or vaginal. The compositions can be formulated for parenteral administration to humans or other mammals in therapeutically effective amounts (eg. amounts which eliminate or reduce the patient's pathological condition) to provide therapy for the neurological diseases described above.

Two of the most convenient administration routes include subcutaneous injection (e.g., dissolved in 0.9% sodium chloride) and oral adminstration (e.g., in a capsule).

GPE analogs may be administered before or after an insult leading to neural injury or neural damage has occurred, or may be administered concurrently with such an insult. For example, GPE analogs may be administered to a patient before a procedure or treatment which carries risk of neural damage in order to reduce or prevent any possible neural injury as result of the procedure or treatment. GPE analogs may also be administered at any time up to and including about 100 hours after an insult to protect neural or glial cells from injury or death. GPE analogs may be particularly effective when administered during a time period including the time between about 0.5 hours to about 8 hours after an insult to protect neural cells from injury or death.

The calculation of the effective amount of GPE analogs to be administered is within the skill of one of ordinary skill in the art, and will be routine to those persons skilled in the art. Needless to say, the final amount to be administered will be dependent upon the route of administration and upon the nature of the neurological disorder or condition that is to be treated. A suitable dose range may for example be between about 0.01 mg to about 1 mg/100 g of body weight, or more specifically about 0.06 µg to 0.6 mg of GPE analog per 100 g of body weight where the dose is administered centrally.

For inclusion in a medicament, GPE analogs can be directly synthesized by conventional methods such as the stepwise solid phase synthesis method of Merryfield et al., 1963 (J. Am. Chem. Soc. 15:2149–2154). Such methods of peptide synthesis are known in the art, and are described, e.g., in Fields and Colowick, 1997, *Solid Phase Peptide Synthesis* (Methods in Enzymology, vol. 289), Academic Press, San Diego, Calif. Alternatively synthesis can involve the use of commercially available peptide synthesizers such as the Applied Biosystems model 430A.

The starting materials and reagents used in preparing these compounds are either available from commercial suppliers such as Aldrich Chemical Company (Milwaukee, Wis.), Bachem (Torrance, Calif.), Sigma (St.Louis, Mo.), or are prepared by methods well known to the person of ordinary skill in the art following procedures described in such references as Fieser and Fieser's Reagents for Organic Synthesis, vols 1–17, John Wiley and Sons, New York, N.Y., 1991; Rodd's Chemistry of Carbon Compounds, vols. 1–5 and supplements, Elsevier Science Publishers, 1989; Organic Reactions, vols. 1–40, John Wiley and Sons, New York, N.Y., 1991; March J; Advanced Organic Chemistry, $4^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art.

The starting materials, intermediates, and compounds of this invention may be isolated and purified using conventional techniques, including filtration, distillation, crystallization, chromatography, and the like. They may be characterized using conventional methods, including physical constants and spectral data. Typically, the reactions described herein take place at atmospheric pressure over a temperature range between about 0° C. and 125° C.

Analogs of GPE, or modifications thereof, such as esters or amides, may in general be prepared by methods such as are already well-known to persons of ordinary skill in the art of peptide and modified peptide synthesis by following other methods well-known to those of ordinary skill in the art of the synthesis of peptides and analogs.

Conveniently, synthetic production of the polypeptide of the invention may be according to the solid phase synthetic method described by Merrifield et al. Solid phase peptide synthesis. I. The synthesis of a tetrapeptide: J. Amer. Chem. Soc. 85, 2149–2156, 1963. This technique is well understood and is a common method for preparation of peptides. The solid phase method of synthesis involves the stepwise addition of protected amino acids to a growing peptide chain which is bound by covalent bonds to a solid resin particle. By this procedure, reagents and by-products are removed by filtration, thus eliminating the necessity of purifying intermediates. The general concept of this method depends on attachment of the first amino acid of the chain to a solid polymer by a covalent bond. Succeeding protected amino acids are added, one at a time (stepwise strategy), or in blocks (segment strategy), until the desired sequence is assembled. Finally, the protected peptide is removed from the solid resin support and the protecting groups are cleaved off.

The amino acids may be attached to any suitable polymer as a resin. The resin must contain a functional group to which the first protected amino acid can be firmly linked by a covalent bond. Various polymers are suitable for this purpose, such as cellulose, polyvinyl alcohol, polymethylmethacrylate, and polystyrene. Suitable resins are commercially available and well known to those of skill in the art. Appropriate protective groups usable in such synthesis include tert-butyloxycarbonyl (BOC), benzyl (Bzl), t-amyloxycarbonyl (Aoc), tosyl (Tos), o-bromo-phenylmethoxycarbonyl (BrZ), 2,6-dichlorobenzyl ($BzlCl_2$), and phenylmethoxycarbonyl (Z or CBZ). Additional protective groups are identified in Merrifield, cited above, as well as in McOmie J F W: Protective Groups in Organic Chemistry, Plenum Press, New York, 1973.

The general procedure of preparation of the peptides of this invention involves initially attaching the protected carboxyl-terminal amino acid to the resin. After attachment the resin is filtered, washed and the protecting group (desirably BOC) on the α-amino group of the carboxyl-terminal amino acid is removed. The removal of this protecting group must take place, of course, without breaking the bond between that amino acid and the resin. The next amino, and if necessary, side chain protected amino acid, is then coupled to the free α-amino group of the amino acid on the resin. This coupling takes place by the formation of an amide bond between the free carboxyl group of the second amino acid and the amino group of the first amino acid attached to the resin. This sequence of events is repeated with successive amino acids until all amino acids are attached to the resin. Finally, the protected peptide is cleaved from the resin and the protecting groups removed to reveal the desired peptide. The cleavage techniques used to separate the peptide from the resin and to remove the protecting groups depend upon the selection of resin and protecting groups and are known to those familiar with the art of peptide synthesis.

Alternative techniques for peptide synthesis are described in Bodanszky et al, Peptide Synthesis, 2nd ed, John Wiley and Sons, New York, 1976. For example, the peptides of the invention may also be synthesized using standard solution peptide synthesis methodologies, involving either stepwise or block coupling of amino acids or peptide fragments using chemical or enzymatic methods of amide bond formation. [See, e.g. H. D. Jakubke in The Peptides, Analysis, Synthesis, Biology, Acadermic Press, New York, 1987, p. 103–165; J. D. Glass, ibid., pp. 167–184; and European Patent 0324659 A2, describing enzymatic peptide synthesis methods.] These solution synthesis methods are well known in the art.

A person of ordinary skill in the art will have no difficulty, taking account of that skill and the knowledge available, and of this disclosure, in developing one or more suitable synthetic methods for compounds of this invention.

For example, analogs in which the glycine residue of GPE is replaced by an alternative amino acid may conveniently be prepared by the preparation of a protected proline-glutamic acid di-peptide (such as the dibenzyl ester), and coupling that dipeptide with a protected glycine analog, followed by deprotection. Analogs in which the glutamic acid residue of GPE is replaced by an alternative amino acid or an amino acid amide or ester may conveniently be prepared by the preparation of a protected glycine-L-proline di-peptide (such as BOC-glycyl-L-proline), and coupling that dipeptide with a protected glutamic acid and esters or glutamine. Where modifications are to be made to two or more amino acids, the coupling techniques will still be the same, with just more than one different amino acid or analog being used in the synthesis. The choice of appropriate protecting groups for the method chosen (solid-phase or solution-phase), and of appropriate substrates if solid-phase synthesis is used, will be within the skill of a person of ordinary skill in the art.

Conjugation and modification of the resulting peptides may be accomplished by standard techniques known in the art. For example, esterification may be used to provide GPE-stearate, and amidation may be used to provide GPE-amide. GPE analogs may be made by conjugating another molecule to GPE. For example, it is known in the art to conjugate polyethylene glycol (PEG) to peptides; such modified peptides are termed PEGylated peptides. PEGylated GPE peptides comprise GPE analogs of the invention, and may be provided using, e.g., the conjugate technology described in WO 95/32003 published Nov. 30, 1995. Various weights of PEG may be used to provide a variety of PEGylated peptide analogs. PEGylated peptides often remain available within a patient for longer times than nonPEGylated peptides.

As a general proposition, the total pharmaceutically effective amount of GPE analog administered parenterally per dose will be in a range that can be measured by a dose response curve. The preferred range will be between about 0.01 mg to about 1 mg per 100 g body weight, specifically between about 0.06 mg/100 g body weight to about 0.6 mg/100 g body weight. For example, GPE analogs in the blood can be measured in body fluids of the mammal to be treated to determine dosing. Alternatively, one can administer increasing amounts of the GPE analog to the patient and check the serum levels of the patient for the GPE analog. The amount of GPE analog to be employed can be calculated on a molar basis based on these serum levels of GPE analog.

Specifically, one method for determining appropriate dosing of the analog entails measuring GPE analog levels in a biological fluid such as a body or blood fluid. Measuring such levels can be done by any means, including RIA and ELISA. After measuring GPE analog levels, the fluid is contacted with the compound using single or multiple doses. After this contacting step, the GPE analog levels are re-measured in the fluid. If the fluid GPE analog levels have fallen by an amount sufficient to produce the desired efficacy for which the molecule is to be administered, then the dose of the molecule can be adjusted to produce maximal efficacy. This method can be carried out in vitro or in vivo. Preferably, this method is carried out in vivo, i.e. after the fluid is extracted from a mammal and the GPE analog levels measured, the analog herein is administered to the mammal using single or multiple doses (that is, the contacting step is achieved by administration to a mammal) and then the GPE analog levels are remeasured from fluid extracted from the mammal.

GPE analogs may also be suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), poly(2-hydroxyethyl methacrylate) (Langer et al., 1981), ethylene vinyl acetate (Langer et al., supra), or poly-D-(-)-3-hydroxybutyric acid (EP 133,988). Sustained-release compositions also include a liposomally entrapped compound. Liposomes containing GPE analogs are prepared by methods known per se: DE 3,218,121; Hwang et al., 1980; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol percent cholesterol, the selected proportion being adjusted for the most efficacious therapy. All documents referred to herein, both supra and infra, are hereby incorporated by reference in their entirety.

For parenteral administration, doses may be between about 0.01 to about 1 mg of GPE analog per 100 g of body weight, more specifically about 0.06 µg to 0.6 mg of GPE analog per 10 g body weight. In one embodiment, the analog is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the compound uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

The GPE analog is typically formulated in such vehicles at a pH of from or about 4.5 to 8. It will be understood that use of certain of the foregoing excipients, carriers, or stabilizers will result in the formation of salts of the compound. The final preparation may be a stable liquid or lyophilized solid.

Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen, or cherry. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent, and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

Typically, the GPE analog to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The GPE analog ordinarily will be stored in unit or multi-dose containers, for example, sealed ampules or vials, as an aqueous solution or as a lyophilized formulation for reconstitution. As an example of a lyophilized formulation, 10 mL vials are filled with 5 ml of sterile-filtered 0.001% (w/v) aqueous solution of compound, and the resulting mixture is lyophilized. The infusion solution is prepared by reconstituting the lyophilized compound using bacteriostatic Water-for-Injection.

EXPERIMENTAL

Experiment 1

Materials and Methods

Synthesis of tritium-labelled GPE ($^3$H-Me-GPE)

A Schiff base formed between formaldehyde and the N-terminal glycine amino group of GPE tripeptide at 0–4° C., pH 8.5 was reduced with high specific activity tritiated sodium borohydride (100 mCi, 50–70 Ci/mM, Amersham, Bucks, UK) resulting in the addition of a stable tritium-bearing methyl group on the free amine of the glycine as described previously (Means, G. E. and Feeney, R. E. in Chemical modification of proteins, Vol 1, 216–217, Holden-day, Inc, San Francisco; Guan et al., 1996, NeuroReport, Vol. 7).

After tritiation the reaction mixture was diluted in ammonium acetate buffer (0.05M, pH 5.5 with 20% v/v methanol, 10 ml) and purified using Accell CM- and QMA+Sep-Paks (Waters, Milford, Mass., USA) in series. After washing with the ammonium acetate buffer to remove reagents and byproducts (tritiated water and tritiated methanol), the CM- and QMA+cartridges were uncoupled and the $^3$H-Me-GPE was eluted from the QMA cartridge with ammonium bicarbonate (0.3M, 6 ml). The eluted material was lyophilized twice to remove the bulk of the ammonium bicarbonate, dissolved in ethanol-water (1:19, 20 μl) and aliquots stored at −70° C.

Animal Preparation

The following experimental protocol followed guidelines approved by the University of Auckland Animal Ethics Committee. Adult male Wistar rats were killed by decapitation and tissues immediately removed and stored at −80° C. Coronal sections (16 μm) were cut on a cryostat and mounted on gelatin-coated slides. Normal adult human postmortem brain (n=4) tissue was cut and mounted in a similar manner.

The optimal protocol for $^3$H-Me-GPE binding was: a 10 minute preincubation in buffer (50 nM Tris-HCl, pH 7.4) with protease inhibitors (20 mM EDTA, 1 mM phenylmethylsulfonyl fluoride, 2 mM N-ethylmaleimide and 5 mM benzamidine), followed by a 90 minute incubation at 24° C. in the same buffer including 50 nM $^3$H-Me-GPE, followed by 2×1 minute washes in ice-cold distilled water and dried in a cold air flow. Non-specific binding was defined by coincubation with the unlabeled ligand (10 μM) and was typically 25–30%.

Results

The results are shown in FIGS. 1 and 2.

The observed distribution of $^3$H-Me-GPE appears to be unique in comparison to that of related ligands (Monaghan, D. T. and Cotman, C. W., J Neuroscience, Vol. 5, 1985; Bohannon et al., Brain Research, Vol. 444, 1988; Wenzel et al., NeuroReport, Vol. 7, 1995). There was intense binding in the CA1-2 region of the hippocampus and lesser binding in the pyriform cortex, amygdala, choroid plexus and large blood vessels (FIG. 1). In comparison to the CA1-2 region of the hippocampus there was less binding in the molecular layer of the dentate gyrus, where glutamate (NMDA) receptors are present at high density (Monaghan, D. T. and Cotman, C. W., J Neuroscience, Vol. 5, 1985). Binding in the CA1-2 region was blocked by an excess (10 μM) of N-methyl-GPE but not by glutamate (1 mM) or by MK-801, NBQX, glycine, nicotine or adenosine (100 μM). The highest binding in the rat brain was seen in the strata radiatum and oriens of CA1. Apart from a trace of binding in the lung and major blood vessels, $^3$H-Me-GPE-binding activity was not detected in any other tissue.

To determine whether there was a similar distribution of binding sites in the human brain autoradiography of $^3$H-Me-GPE was performed on sections spanning the hippocampus and entorhinal cortex. The highest binding was observed in the molecular layer of the dentate gyrus and the CA1-2 region of the hippocampus (FIG. 2).

Experiment 2

Materials and Methods

Tritiated GPE (Gly-[$^3$H]Pro-Glu, 1.6 ml, specific activity 50–60 Ci/mmol) obtained from Sibtech, Inc., USA was used in these experiments.

Animal Preparation

The following experimental protocol followed guidelines approved by the University of Auckland Animal Ethics Committee.

Cardiac Administration

Adult Wistar rats (300 g) were prepared under halothane/$O_2$ anaesthesia. The rats were randomly assigned to one of four groups: tritiated GPE, saline+0.1% BSA, tritiated GPE+non-tritiated GPE or tritiated proline. Rats in the tritiated GPE, tritiated proline and control groups were sacrificed at 30 min, 1 hr or 6 hrs after administration. Rats co-administered with both tritiated and non- tritiated GPE were sacrificed at 10 minutes after administration. For all groups, tissue was homogenized in Soluene® (a tissue solubilizer; Packard Bioscience Company, Meriden Conn.) and counted in a β counter.

V and IP Administration

Rats were injected with 10 million counts of tritiated GPE in 500 μl total (made up with 0.1% BSA in saline). Animals were sacrificed at 30 minutes, 1, 3 or 6 hrs. Tissue was homogenized in Soluene® and counted in a β counter.

ICV Administration

Adult Wistar rats (300 g) were prepared under halothane/$O_2$ anaesthesia. A guide cannula was placed on the dura 7.5 mm anterior from stereotaxic zero and 1.5 mm from midline on the right. One million counts of GPE and 600 μl of non-tritiated GPE were injected in 8 μl total volume (made up with 0.1% BSA in saline). Rats were sacrificed 30 minutes after administration. Tissue was homogenized in Soluene® and counted in a β counter.

Tritiated GPE, tritiated GPE+non-tritiated GPE, tritiated proline (Amersham) or tritiated proline+non-tritiated proline in vehicle (0.1M citrate buffer [pH6], diluted 10 times in 0.1% bovine serum albumin in 0.1M phosphate buffered saline [PBS] [pH7.3]) were then given by different routes of administration to injured and non-injured rats according to the following study design:

1) cardiac puncture:

| | |
|---|---|
| tritiated GPE | 10 million counts (20 μl in 300 μl) |
| tritiated and non-tritiated GPE | 10 million counts + 600 μg |
| tritiated proline | 10 million counts |
| Saline + 0.1% BSA | 200 μl |

2) intravenously (iv):

| | |
|---|---|
| tritiated GPE | 10 million counts |
| Saline + 0.1% BSA | 200 μl |

3) intraperitoneally (ip):

| | |
|---|---|
| tritiated GPE | 10 million counts |
| Saline + 0.1% BSA | 200 μl |

4) intracerebroventricularly (icv):

| | |
|---|---|
| tritiated GPE | 1 million counts |
| tritiated and non-tritiated GPE | 1 million counts + 600 μg |

The following describes the various methods of the routes of administration for the administration of the following solutions: tritiated GPE, tritiated GPE+non-tritiated GPE, tritiated proline, or tritiated proline+non-tritiated proline.

Cardiac administration was performed using a syringe. The syringe needle was placed into the left ventricle and one of the above four solutions was given.

IV administration was carried out by injecting one of the four solutions into the tail vein.

IP administration was performed by injecting one of the four solutions into the peritoneal cavity.

ICV administration was carried out according to the following procedure. The rats were lightly anaesthetized again using 0.15 ml Saffan™ (Pitman-Moore Ltd, NZ). The infusion of one of the four solutions was made into the right lateral ventricle guided by a metal cap fitted over the rat head using a modified technique originally described by Jirikowski (J Neuroscience Methods, 42: 115–118, 1992), in order to ensure correct placement of the infusion needle. One of the four solutions was administered in a single dose.

The rats were sacrificed using pentobarbital 10, 60 or 360 minutes after administration of either tritiated GPE or tritiated proline. The distribution of administered tritiated GPE or proline was ascertained. Counts/minute/mg were made in the following tissues: kidney, blood, adrenal glands, liver, lung, testicle, heart, muscle, spinal cord and brain. HPLC was used in order to check that the particles counted were either tritiated GPE or tritiated proline.

Results

Figure 3:
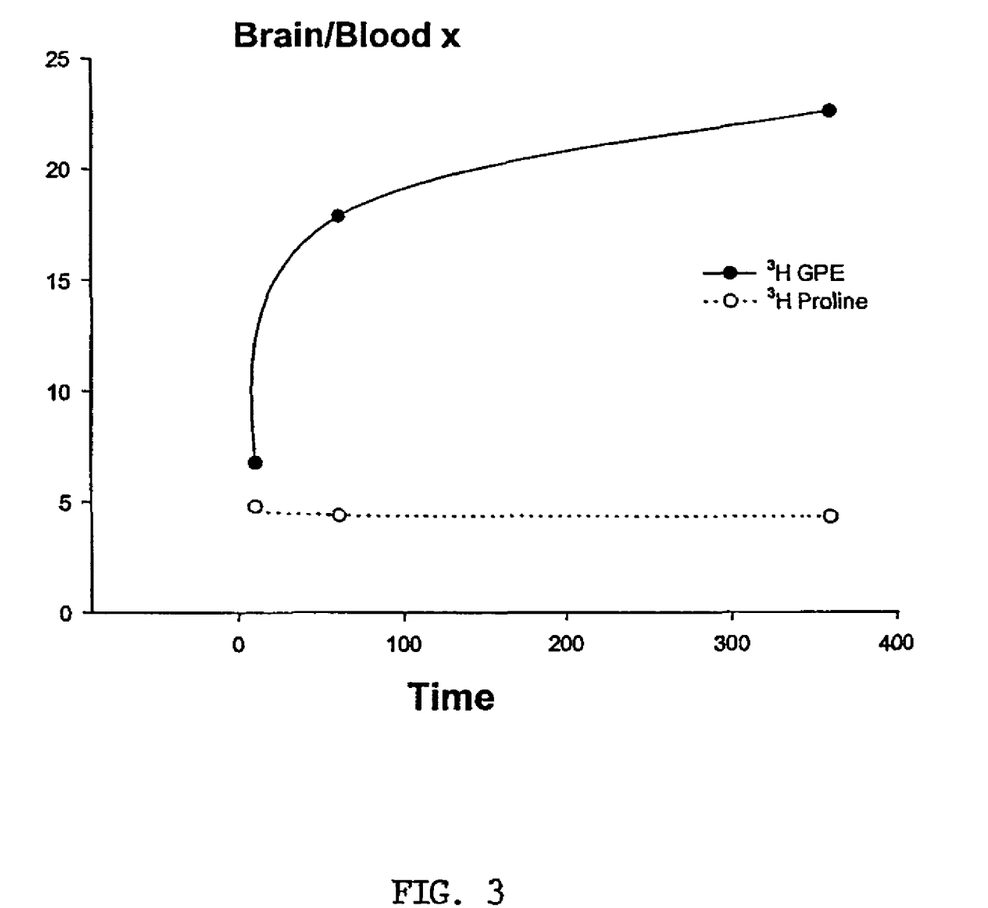
FIG. 3 is a graph showing accumulation of tritiated GPE in the brain over time.

The amount of tritiated GPE increases over time in the brain relative to the blood (FIG. 3). With cardiac administration 60 minutes was the time-point at which there was the most tritiated GPE in the brain.

When tritiated and non-tritiated GPE were administered both together via cardiac administration the only displacement of GPE occurred in the brain. This result was supported by ICV administration.

Furthermore, using ICV administration GPE was found to be selectively taken up on the injured side of the brain in rats with an hypoxic-ischemic brain injury.

With ip administration the amount of GPE in the brain compared to the corresponding time-points after iv and cardiac injection was increased.

These results therefore show the ability of GPE to pass through the blood-brain-barrier, including in the absence of neural insult.

Experiment 3

Materials and Methods

This experiment involved treating rats with a control vehicle or GPE administered peripherally 2 hours after a focal CNS injury. The rats had an hypoxic-ischemic injury to one cerebral hemisphere induced in a standard manner (ligation of the carotid artery). The degree and length of hypoxia, the ambient temperature and humidity were defined to standardize the degree of damage. The neuronal death is restricted to the side of the carotid ligation and is primarily in the hippocampus, dentate gyrus, striatum and lateral cortex of the ligated hemisphere. There is no neuronal loss in the contralateral hemisphere.

Specifically forty-nine 50–60 day old adult Wistar rats (280–310 g) were prepared under halothane/$O_2$ anaesthesia. The right side carotid artery was ligated. The rats were allowed to recover for 1 hour and were then placed in an incubator with humidity 90±5% and temperature 31±0.5° C. for 1 hour before hypoxia. Oxygen concentration was reduced and maintained at 6±0.2% $O_2$ for 10 minutes. The rats were kept in the incubator for 2 hours after hypoxia and then treated either with 5mg GPE administered intraperitoneally or vehicle alone (saline+0.1% BSA). The rats were sacrificed using pentobarbital 7 days after hypoxic-ischemic injury.

The rats were transcardially perfised with 0.9% saline followed by 4% paraformaldehyde, and the brains were removed and embedded in paraffin. Symmetric serial coronal sections (4 µm) were cut and stained with thionin/acid-fuchsin for live/dead neurons (Sirimanne et al., 1994 *Journal of Neuroscience*, 55: 7–14). The histological outcome of neuronal survival was examined with light microscopy (Leica) in the hippocampus in the injured hald of the brain according to a reference of rat brain anatomy (Paxinos, and Watson (1982) The rat brain in stereotaxic coordinates, $2^{nd}$ Edition, Academic Press, New York, USA). Only cells with a morphology like live neurons were counted, while dead neurons or cells with morphology like glia were not included. One coronal section was used for each brain.

A coronal section (A-P 4.5 mm) was used for analysis of the hippocampus. All surviving neurons in the hippocampal CA1/2 region of the injured hemisphere were counted. Data were analysed with paired t-test and presented as mean±sem (standard error of the mean).

Results

Figure 4:
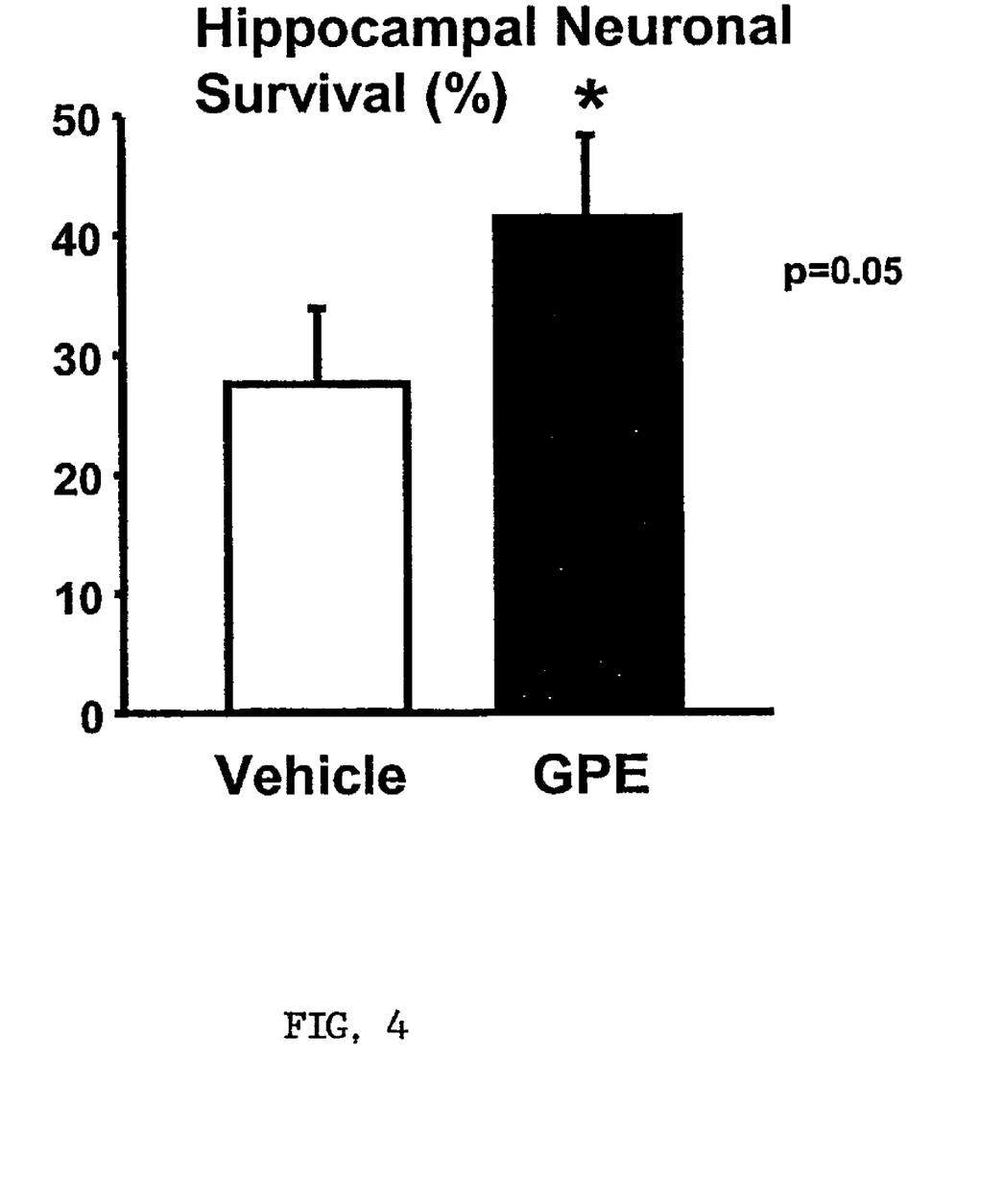
FIG. 4 shows the effect of GPE administered peripherally on neuronal survival after an hypoxic-ischemic injury.

The results are shown in FIG. 4.

GPE administered peripherally increases neuronal survival in the hippocampus after an hypoxic-ischemic injury.

These results establish a neural bioactivity profile for GPE against which a candidate analog can be compared.

UTILITY

Thus, in accordance with the present invention there are provided GPE analogs. These analogs have application in any method of therapy or prophylaxis in which GPE has application. These include the treatment of acute brain injury and neurodegenerative disease, including but not limited to injury or disease in the CNS.

In addition, the ability of the GPE analogs to cross the blood brain barrier allows them to be administered peripherally to a patient in need of treatment in the brain.

As with GPE, the analogs will normally be administered as part of a pharmaceutical composition or preparation.

Those persons skilled in the art will appreciate that the present invention is described above by way of example only and is not intended to be limited to the specific experimental details given.

We claim:

1. An analog of the tripeptide, Gly-Pro-Glu (GPE), wherein said Gly is replaced by Ala thereby fanning L-Ala-PE.

2. A method of treating a medical condition resulting from neural injury or disease, comprising administering an effective amount of L-Ala-PE.

3. The method of claim 2, wherein said medical condition is associated with hypoxic-ischemic injury.

4. The method of claim 2, wherein said disease is multiple sclerosis.

5. The method of claim 2, wherein said L-Ala-PE is administered at any time up to and including about 100 hours after said neural injury or disease.

6. The method of claim 2, wherein said L-Ala-PE is administered prophylactically.

7. The method of claim 2, wherein said medical condition results from a procedure likely to produce acute brain injury.

8. The method of claim 7, wherein said L-Ala-PE is administered prior to said procedure.

9. A pharmaceutical composition comprising L-Ala-Pro-Glu (L-Ala-PE) and a pharmaceutically acceptable carrier.

10. The pharmaceutical composition of claim 9, and a pharmaceutically acceptable excipient.

11. A method of protecting neuronal cells in a patient from damage likely to result in neural injury or disease, comprising administering to said patient a therapeutic amount of a GPE analog of claim 1.

12. The method of claim 11, wherein said cells are neural cells.

13. The method of claim 11, wherein said damage is associated with an elective procedure.

14. The method of claim 11, wherein said L-Ala PE is included with a pharmaceutically acceptable excipient as a pharmaceutical composition.

15. A pharmaceutical composition comprising the analog of claim 1, and at least one pharmaceutically acceptable excipient selected from the group consisting of water, Ringer's solution, dextrose, phosphate buffer, citrate buffer, succinate buffer, acetic acid buffer, an antioxidant, peptides having a less than about 10 amino acid residues, polyarginine, tripeptides, serum albumin, gelatin, immunoglobulin, polyvinylpyrrolidone, glycine, amino acid, monosaccharide, disaccharide, cellulose, glucose, mannose, trehalose, dextrins, chelating agents, sugar alcohols, counter ions, non-ionic surfactants and neutral salts.

16. The pharmaceutical composition of claim 9, wherein said pharmaceutical composition is adapted for peripheral administration.

17. The pharmaceutical composition of claim 9, wherein said pharmaceutical composition is adapted for intrathecal administration.

18. The method of claim 11, wherein the route of administration is by implant, aerosol, inhalation, scarification, intraperitoneal, subcutaneous, intracapsular, intramuscular, intranasal, oral, buccal, pulmonary, rectal, vaginal or intravenous.

19. The method of claim 11, wherein said GPE analog is administered in a dose range of:

from about 0.01 mg/100 g body weight;

to about 1 mg/100 g body weight.

20. The method of claim 11, wherein said damage is associated with an elective surgical procedure.

21. The pharmaceutical composition of claim 9, in a capsule.

* * * * *

UNITED STATES PATENT AND TRADEMARK OFFICE
CERTIFICATE OF CORRECTION

| | |
|---|---|
| PATENT NO. | : 7,112,570 B2 |
| APPLICATION NO. | : 10/362266 |
| DATED | : September 26, 2006 |
| INVENTOR(S) | : Peter Gluckman and Tajrena Elexi |

It is certified that error appears in the above-identified patent and that said Letters Patent is hereby corrected as shown below:

Col. 13, line 21, after "having" and before "less" delete "a".

Signed and Sealed this

Sixth Day of March, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,112,570 B2 |
| APPLICATION NO. | : 10/362266 |
| DATED | : September 26, 2006 |
| INVENTOR(S) | : Peter Gluckman et al. |

It is certified that error appears in the above-identified patent and that said Letters Patent is hereby corrected as shown below:

In the Claims:

Col. 12, line 50: Delete "fanning" and insert --forming--.

Signed and Sealed this

Twenty-ninth Day of July, 2008

JON W. DUDAS
*Director of the United States Patent and Trademark Office*